United States Patent
Lynn et al.

(10) Patent No.: US 9,651,483 B1
(45) Date of Patent: May 16, 2017

(54) COMPOSITIONS OF INORGANIC LUMINESCENT MATERIALS

(71) Applicant: Washington State University, Pullman, WA (US)

(72) Inventors: Kelvin Lynn, Pullman, WA (US); Drew Haven, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 540 days.

(21) Appl. No.: 14/215,841

(22) Filed: Mar. 17, 2014

Related U.S. Application Data (60) Provisional application No. 61/786,303, filed on Mar. 15, 2013.

(51) Int. Cl.
| | |
|---|---|
| *G01T 1/16* | (2006.01) |
| *G01T 1/202* | (2006.01) |
| *H01J 29/30* | (2006.01) |
| *G01N 21/53* | (2006.01) |
| *G01N 21/09* | (2006.01) |

(52) U.S. Cl.
CPC .......... *G01N 21/53* (2013.01); *G01N 21/09* (2013.01); *G01T 1/16* (2013.01); *G01T 1/202* (2013.01); *H01J 29/30* (2013.01)

(58) Field of Classification Search
CPC .......... G01T 1/16; G01T 1/202; H01J 29/30
See application file for complete search history.

(56) References Cited

U.S. PATENT DOCUMENTS

| | | | |
|---|---|---|---|
| 5,004,948 A * | 4/1991 | Kinczel ........... | C04B 35/44 252/301.4 R |
| 2008/0187746 A1 | 8/2008 | De Graaf et al. | |
| 2011/0006449 A1* | 1/2011 | Mukherjee ........... | B82Y 30/00 264/10 |

FOREIGN PATENT DOCUMENTS

GB 1076643 A 7/1967

* cited by examiner

*Primary Examiner* — David Porta
*Assistant Examiner* — Faye Boosalis
(74) *Attorney, Agent, or Firm* — Whitham, Curtis & Cook (57) ABSTRACT

Disclosed herein are material compositions that include a metal doped, alumina rich yttrium aluminum garnet (YAG:M). Also provided according to embodiments of the invention are scintillator compositions that include $Y_{3-x}M_xAl_{5+y}O_{12+z}$, as a primary phosphor and wherein $0 \leq x < 0.03$, $0.001 < y < 0.2$ and $0 \leq z < 0.012$, or $0 \leq x < 0.01$, $0.001 < y < 0.1$ and $0 \leq z < 0.0625$ and M comprises elements selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu). and can include a single or a mixture of a these elements.

7 Claims, 6 Drawing Sheets

COMPOSITIONS OF INORGANIC LUMINESCENT MATERIALS

PRIORITY INFORMATION

The present application claims priority to U.S. Provisional Patent Application Ser. No. 61/786,303 of Kelvin Lynn and Drew Haven titled "CE DOPED YAG" filed on Mar. 15, 2013, the disclosure of which is incorporated herein by reference.

FEDERALLY SPONSORED RESEARCH

The invention was made with Government support under Domestic Nuclear Detection Office, Award No. 2009-DN-077-ARI029-02. The Government has certain rights in the invention.

FIELD OF THE INVENTION

The present invention relates to phosphor compositions and to light emitting devices that include phosphor compositions.

BACKGROUND

Light emitting diodes ("LEDs") are well known solid state lighting devices that are capable of generating light. LEDs generally include a plurality of semiconductor layers that may be epitaxially grown on a semiconductor or non-semiconductor substrate such as, for example, sapphire, silicon, silicon carbide, gallium nitride or gallium arsenide substrates. One or more semiconductor active layers are formed in these epitaxial layers. When a sufficient voltage is applied across the active layer, electrons in the n-type semiconductor layers and holes in the p-type semiconductor layers flow toward the active layer. As the electrons and holes flow toward each other, some of the electrons will "collide" with a hole and recombine. Each time this occurs, a photon of light is emitted, which is how LEDs generate light. The wavelength distribution of the light generated by an LED generally depends on the semiconductor materials used and the structure of the thin epitaxial layers that make up the "active region" of the device (i.e., the area where the electrons and holes recombine).

LEDs typically have a narrow wavelength distribution that is tightly centered about a "peak" wavelength (i.e., the single wavelength where the radiometric emission spectrum of the LED reaches its maximum as detected by a photodetector). For example, the spectral power distributions of a typical LED may have a full width of, for example, about 10-30 nm, where the width is measured at half the maximum illumination (referred to as the full width half maximum or "FWHM" width). Accordingly, LEDs are often identified by their "peak" wavelength or, alternatively, by their "dominant" wavelength. The dominant wavelength of an LED is the wavelength of monochromatic light that has the same apparent color as the light emitted by the LED as perceived by the human eye. Thus, the dominant wavelength differs from the peak wavelength in that the dominant wavelength takes into account the sensitivity of the human eye to different wavelengths of light.

As most LEDs are almost monochromatic light sources that appear to emit light having a single color, LED lamps that include multiple LEDs that emit light of different colors have been used in order to provide solid state light emitting devices that generate white light. In these devices, the different colors of light emitted by the individual LED chips combine to produce a desired intensity and/or color of white light. For example, by simultaneously energizing red, green and blue light emitting LEDs, the resulting combined light may appear white, or nearly white, depending on the relative intensities of the source red, green and blue LEDs.

White light may also be produced by surrounding a single-color LED with a luminescent material that converts some of the light emitted by the LED to light of other colors. The combination of the light emitted by the single-color LED that passes through the wavelength conversion material along with the light of different colors that is emitted by the wavelength conversion material may produce a white or near-white light. For example, a single blue-emitting LED chip (e.g., made of indium gallium nitride and/or gallium nitride) may be used in combination with a yellow phosphor, polymer or dye. Blue LEDs made from indium gallium nitride exhibit high efficiency (e.g., external quantum efficiency as high as 60%). In a blue LED/yellow phosphor lamp, the blue LED chip produces an emission with a dominant wavelength of about 445-470 nanometers, and the phosphor produces yellow fluorescence with a peak wavelength of about 550 nanometers in response to the blue emission. Some of the blue light passes through the phosphor (and/or between the phosphor particles) without being down-converted, while a substantial portion of the light is absorbed by the phosphor, which becomes excited and emits yellow light (i.e., the blue light is down-converted to yellow light). The combination of blue light and yellow light may appear white to an observer. Such light is typically perceived as being cool white in color. In another approach, light from a violet or ultraviolet emitting LED may be converted to white light by surrounding the LED with multicolor phosphors or dyes. In either case, red-emitting phosphor particles (e.g., a $CaAlSiN_3$ ("CASN") based phosphor) may also be added to improve the color rendering properties of the light, i.e., to make the light appear more "warm," particularly when the single color LED emits blue or ultraviolet light.

LEDs are used in a host of applications including, for example, backlighting for liquid crystal displays, indicator lights, automotive headlights, flashlights, specialty lighting applications and even as replacements for conventional incandescent and/or fluorescent lighting in general lighting and illumination applications. In many of these applications, it may be desirable to provide a lighting source that generates light having specific properties.

LEDs are a class of luminescent materials: those that absorb energy in one portion of the electromagnetic spectrum and emits energy in another portion of the electromagnetic spectrum. A luminescent material in powder form is commonly called a phosphor, while a luminescent material in the form of a transparent solid body is commonly called a scintillator. Thus a powder form of a scintillator may be referred to as a phosphor.

Most useful phosphors emit radiation in the visible portion of the spectrum in response to the absorption of the radiation which is outside the visible portion of the spectrum. Thus, the phosphor performs the function of converting electromagnetic radiation to which the human eye is not sensitive into electromagnetic radiation to which the human eye is sensitive. Most phosphors are responsive to more energetic portions of the electromagnetic spectrum than the visible portion of the spectrum. Thus, there are phosphors which are responsive to ultraviolet light (as in fluorescent lamps), electrons (as in cathode ray tubes) and x-rays (as in radiography).

The material properties of scintillators vary greatly based on the specific chemical composition of the scintillator. These properties include scintillator efficiency, primary decay time, afterglow, hysteresis, luminescent spectrum, x-ray stopping power, and resistance to radiation damage. The efficiency of a luminescent material is the percentage of the energy of the absorbed stimulating radiation which is emitted as luminescent light. When the stimulating radiation is terminated, the luminescent output from a scintillator decreases in two stages. The first of these stages is a rapid decay from the full luminescent output to a low, but normally non-zero, value at which the slope of the decay changes to a substantially slower decay rate. This low intensity, normally long decay time luminescence, is known as afterglow. Specifically, afterglow is the light intensity emitted by the scintillator at 100 milliseconds after the x-ray excitation ceases, reported as a percentage of the light emitted while the scintillator is excited by the radiation. Afterglow provides a background luminescent intensity, which is a noise contribution to the photodetector output. In some cases, afterglow is increased by the presence of impurities, and in other cases, afterglow is decreased by the presence of impurities.

Yttrium aluminum garnet ($Y_3Al_5O_{12}$ or YAG) has long been used in many industrial applications. When doped with cerium and most often used for phosphors though also used for scintillators, the Ce undergoes a 5d to 4f transition resulting in broad band yellow light centered at 550 nm. Many metal doped YAG materials display a similar luminescent property. Recently, several studies have demonstrated significant UV defect luminescence centered around 300 nm under cathodoluminescence and ionizing radiation. This limits the efficiency of the cerium luminescence at 550 nm and hinders desired scintillation emission in the visible spectrum.

UV defect emission has been attributed in the past to one or more of several intrinsic defects; however, the prevailing thought now suggests yttrium on aluminum antisites ($Y_{Al}^{3+}$) as the primary defect responsible. Unfortunately, antisites have been shown to be the most energetically favorable intrinsic defect in YAG. Further, $Y_{Al}^{3+}$ on the aluminum octahedral site is the most likely intrinsic defect to be thermally produced in melt grown YAG as it is much more energetically preferable to the opposite antisite, $Al_Y^{3+}$.

Therefore it would be desirable to develop compositions of inorganic luminescent materials with decreased UV defect emission.

SUMMARY

According to some embodiments of the invention, provided are luminescent inorganic material compositions that include a metal doped, Alumina rich yttrium aluminum garnet (YAG:M). Also provided according to embodiments of the invention are luminescent inorganic material compositions that include $Y_{3-x}M_xAl_{5+y}O_{12+z}$, as a primary phosphor and wherein $0 \leq x < 0.03$, $0.001 < y < 0.2$ and $0 \leq z < 0.012$, or $0 \leq x < 0.01$, $0.001 < y < 0.1$ and $0 \leq z < 0.0625$ and, when present, M comprises elements selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu). and can include a single or a mixture of a these elements. Methods of forming a luminescent inorganic material comprising; providing a mixture of $Y_2O_3$, and $Al_2O_3$ in a Y:Al molar ratio of between 1.5:2.5 and 1.5:2.75; heating the mixture to a liquid state; and solidifying the said mixture to form the luminescent inorganic material wherein the method enables the reduction of the frequency of $Y^{3+}_{Al}$ antisites. In particular embodiments a metal oxide dopant is included in the mixture in a Y:M molar ratio of between 1.5:0.0015 and 1.5:0.15 and M is selected from, cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu) or combinations thereof.

DETAILED DESCRIPTION

The present invention now will be described more fully hereinafter with reference to the accompanying drawings, in which particular examples are shown. However, this invention should not be construed as limited to the embodiments set forth herein. Rather, these embodiments are provided so that this disclosure will be thorough and complete, and will fully convey the scope of the invention to those skilled in the art. As used herein the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that, when used in this specification, the terms "comprises" and/or "including" and derivatives thereof, specify the presence of stated features, operations, elements, and/or components, but do not preclude the presence or addition of one or more other features, operations, elements, components, and/or groups thereof.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

In case of conflicting terminology or scope, the present application is controlling.

As used herein, the term "solid state light emitting device" may include a light emitting diode, laser diode, scintilator and/or other semiconductor device which includes one or more semiconductor layers, which may include silicon, silicon carbide, gallium nitride and/or other semiconductor materials, an optional substrate which may include sapphire, silicon, silicon carbide and/or other microelectronic substrates, and one or more contact layers which may include metal and/or other conductive materials. The design and fabrication of solid state light emitting devices are well known to those skilled in the art. The expression "light emitting device," as used herein, is not limited, except that it be a device that is capable of emitting light.

According to some embodiments of the invention, provided are luminescent inorganic material compositions that include a Cerium doped, Alumina rich yttrium aluminum garnet (YAG:M). Also provided according to embodiments of the invention are phosphor compositions that include $Y_{3-x}M_xAl_{5+y}O_{12+z}$, as a primary phosphor, and wherein $0 \leq x < 0.03$, $0.001 < y < 0.2$ and $0z < 0.012$, or $0 \leq x < 0.01$, $0.001 < y < 0.1$ and $0 < z < 0.0625$ and M, when present, comprises elements selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu). and can include a single or a mixture of a these elements. Methods of forming a luminescent inorganic material comprising; providing a mixture of $Y_2O_3$, and $Al_2O_3$ in a Y:Al molar ratio of between 1.5:2.5 and 1.5:2.75; heating the mixture to a liquid state; and solidifying the said mixture to form the luminescent inorganic material wherein the method enables the reduction of the frequency of $Y^{3+}_{Al}$ antisites. In particular embodiments a metal oxide dopant is included in the mixture in a Y:M molar ratio of between 1.5:0.0015 and 1.5:0.15 and M is selected from, cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu) or combinations thereof.

The term "primary phosphor" means that the metal doped YAG, such as $Y_{3-x}M_xAl_{5+y}O_{12+z}$, present in the phosphor compositions described herein. The metal doped YAG phosphor may be the only phosphor in the composition, or the phosphor composition may include additional phosphors.

The inorganic luminescent materials described herein are preferably grown as a materials can be grown as a single crystal material via any of conventional methods that are known to the art. Example methods include, but are not limited to: Czochralski method (CZ), Bridgman method (BG), the micro pulling down method, and Flux growth methods which are conventional methods known in the art. Generally, the elementally pure (~99.99%) oxide powders of the component metal elements of the YAG:M (i.e. $Y_2O_3$, $Al_2O_3$ and the appropriate oxide of the metal dopant) as mixed or milled in the desired elemental ratio and heated to yield a molten mixture that is subsequently cooled at a control led rate.

YAG is represented as a line compound in the $Al_2O_3$—$Y_2O_3$ phase diagram suggesting deviations from where excess oxides favor antisite production rather than vacancies or interstitials. The above findings substantiate several sources that could neither identify $Al_Y^{3+}$ defects within their samples, nor demonstrate they did not readily form. Therefore, off stoichiometric YAG single crystals can and do form; being facilitated by relatively easy $Y_{Al}^{3+}$ production. Excess oxides preferentially form antisites over other intrinsic defects and off stoichiometric YAG confirms $Al_Y^{3+}$ antisites do not readily form. Herein off stoichiometric melts as a method for modifying equilibrium $Y_{Al}^{3+}$ concentrations are disclosed. These off stoichiometric melts yield luminescent inorganic material compositions that optionally include a metal (M) dopant, of which comprises elements that can include, but is not strictly limited to, cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu).

Moreover, such melts can include a single or a mixture of a these elements, such as, for example, an alumina rich yttrium aluminum garnet of the general formula: $Y_{3-x}M_xAl_{5+y}O_{12+z}$, as a primary phosphor, and wherein $0 \leq x < 0.03$ $0.001 < y < 0.2$ and $0 \leq z < 0.012$, or $0 \leq x < 0.01$, $0.001 < y < 0.1$ and $0 \leq z < 0.0625$ Also provided according to some embodiments of the present invention are light emitting devices that include a solid state lighting source; and a phosphor composition according to an embodiment of the invention. In some embodiments, the phosphor composition down-converts radiation having a peak wavelength in a range of 445 nm to 470 nm to radiation having a peak wavelength in a range of 500 nm to 570 nm. In some embodiments, the phosphor compositions can include a secondary phosphor that down-converts radiation having a peak wavelength in a range of 445 nm to 470 nm to radiation having a peak wavelength in a range of 600 nm to 660 nm. In some embodiments, the light emitting device includes a separate secondary phosphor composition such that the phosphor composition and the secondary phosphor composition together down-converts radiation having a peak wavelength in a range of 445 nm to 470 nm to radiation having a peak wavelength in a range of 600 nm to 660 nm. In some embodiments, the phosphor composition is present as a single crystal phosphor.

In particular cases, the luminescent inorganic material compositions may serve as a scintilator material in a detection system.

In some embodiments of the invention, the phosphor composition down-converts at least some of the radiation emitted by the solid state lighting source to a radiation having a peak wavelength greater than 580 nanometers. In some embodiments, the phosphor composition down-converts at least some of the radiation emitted by the solid state lighting source to a radiation having a peak wavelength between 530 nanometers and 585 nanometers, and at least some of the radiation emitted by the solid state lighting source to a radiation having a peak wavelength between 600 nanometers and 660 nanometers.

In some embodiments of the invention, the solid state lighting source comprises a light emitting diode that emits light having a dominant wavelength in the blue color range. In particular embodiments, the dominant wavelength of the blue LED is between about 445 nm to 470 nm.

The present invention will be more fully understood by reference to the following examples, which are intended to be illustrative of the present invention, but not limiting thereof.

EXAMPLES

Five YAG boules were grown under similar conditions by the CZ method. Cerium concentrations were held to 1.0 at. % with respect to yttrium concentrations in an on stoichiometric charge. Melt stoichiometry was varied in 5.0 at. % increments from 10.0 at. % yttria rich to 10.0 at. % alumina rich. The starting materials used were high purity yttria ($Y_2O_3$, 99.999%), alumina ($Al_2O_3$, 99.997%), and $Ce^{+4}$ oxide ($CeO_2$, 99.99%). The powders were weighed with 10 mg precision (adjusting for inherent moisture content in the powders) to a target weight of 400 g, then ball milled using high purity (99.8%) alumina milling balls for 18 hours. After mixing, the powders were compressed in an isostatic press to ~20 kpsi and then calcined at 1400° C. for 15 hours to make the final charge. Upon calcining, the charges lost an average of ~0.77% of their weight from moisture losses.

The crystals were grown with an iridium crucible (86 mm outside diameter by 60 mm high) using a RF induction furnace operating at 20 kHz and an atmosphere of ~100 ppm oxygen balanced with nitrogen. First, one charge was melted over the course of ~5 hours and then cooled. After this, a second like charge was added to the crucible to increase the melt volume to 800 g to improve heat flow and maintain stable flow patterns during growth. The crystal was pulled using a 6 mm diameter, (111) orientation, undoped YAG rod at 2 mm/hr to grow the cone of the crystal, then 1 mm/hr to grow the full diameter section. The crucible and melt were rotated at 6 RPM while the pulling arm was not rotated. Weight was monitored through the pulling arm and adjusted via a PID controller. Each boule was ~32 mm in diameter and between 116-126 min in length.

Figure 1:
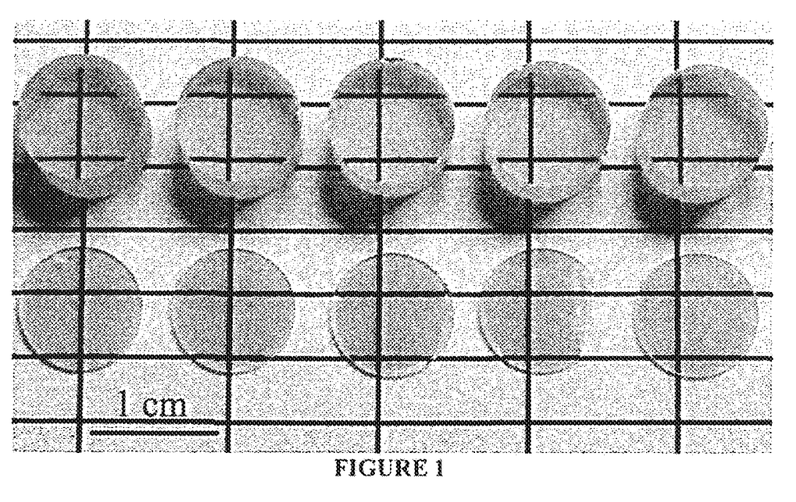
FIG. 1—From left to right, samples from 10.0 at. % yttria rich, 5.0 at. % yttria rich, on stoichiometry, 5.0 at. % alumina rich, and 10.0 at. % alumina rich melts. Some cracks were caused by cutting and polishing.
Figure 2:
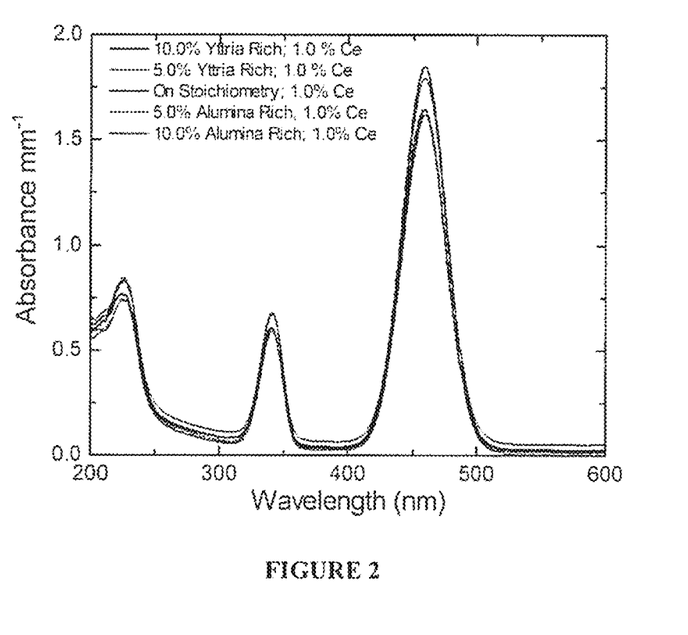
FIG. 2—Absorption of each sample. 1.0 at. % Ce displays good consistency among all of the samples, minimizing concerns of Ce concentration variability on further measurements.

Right cylinders were cut from the bottom half (last to grow) of the untreated boules of Ø10 mm by 10 mm thick with a bordering Ø10 mm by 1 mm sample cut for absorption and transmission measurements. A thin sample assured cerium lines would not become saturated in optical absorption measurements. Each sample was cored from a stress free region as observed using crossed polarizers. Once cut and mechanically polished to a final grit of 0.3 µm (FIG. 1), an Ocean Optics PC2000® Spectrometer using a deuterium light source measured Ce intensity in the 1 mm thick samples (FIG. 2). Ce concentrations displayed good consistency with a Gaussian fit of the 460 nm peak varying by no more than 8% from the mean area of 71.5. (Table I) The small fluctuations observed were consistent with Ce segregation related variation due to small differences in the coring location between samples.

TABLE I

Characteristics of the as grown samples. The largest improvements can be seen with the 10.0 at % alumina rich melt grown sample.

|  | 10.0 at. % Y Rich Melt | 5.0 at. % Y Rich Melt | On Stoichiometry | 5.0 at. % Al Rich Melt | 10.0 at. % Al Rich Melt |
|---|---|---|---|---|---|
| PMT Resolution at 662 keV (%) | 10.4 ± 0.08 | 10.35 ± 0.07 | 9.92 ± 0.07 | 10.56 ± 0.08 | 10.67 ± 0.08 |
| PD Resolution at 662 keV (%) | 9.52 ± 0.08 | 9.8 ± 0.05 | 9.49 ± 0.05 | 9.31 ± 0.05 | 8.19 ± 0.04 |
| PL Counts at 300 nm Peak | $2.99 \times 10^4$ | $2.57 \times 10^4$ | $2.04 \times 10^4$ | $1.82 \times 10^4$ | $1.47 \times 10^4$ |
| 460 nm Absorption Area | 68.8 | 69.2 | 77.2 | 73.9 | 68.0 |

Figure 3:
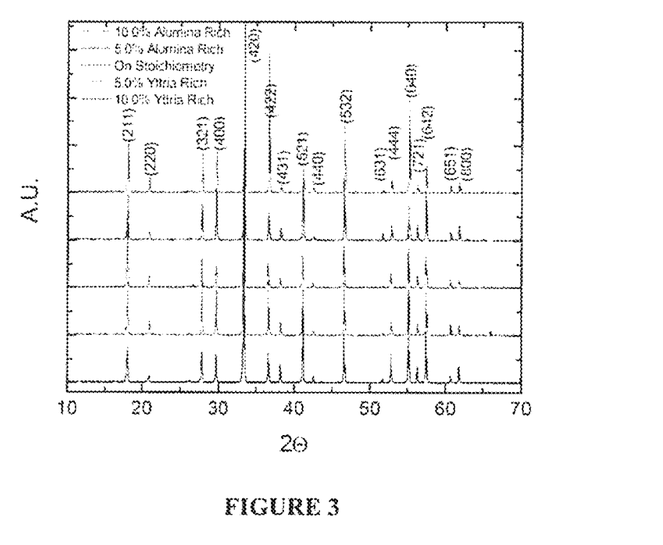
FIG. 3—XRD spectrum from the region immediately surrounding our samples, with peaks indicating a pure YAG phase. The excellent consistency between each sample indicates minimal, if any, contamination from secondary phases.

X-Ray Diffraction (XRD) was performed with a Siemens Kristalloflex powder XRD analyzer to investigate secondary phases. All sections used for XRD were cut from the low stress region surrounding the cored samples to ensure relevance to the tested pieces and were powdered using a porcelain mortar and pestle. Each sample (FIG. 3) exhibited identical peaks corresponding to pure YAG phase planes. No secondary peaks were clearly evident above background noise, meaning secondary phase contamination (excess oxides) was below the detection limit (<1%).

Figure 4:
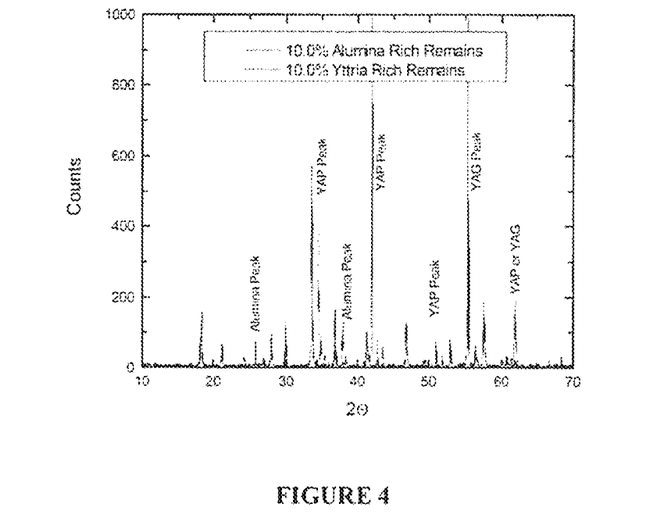
FIG. 4—XRD from the crucible remnants of the 10.0 at. % alumina and yttria rich samples. Alumina rich displays residual alumina, and yttria rich displays significant concentrations of YAP.

To confirm the measurement, crucible remnants were also tested. FIG. 4 demonstrates a significant, though not unexpected, difference between the yttria rich and alumina rich melts which showed differing amounts of remaining oxides. When the melt became yttria rich, XRD of the remaining material showed a large amount of yttrium aluminum perovskite (YAP) not present in the alumina rich melt remnants. When the melt became alumina rich, XRD of the remaining material showed excess alumina. This is expected based on the alumina-yttria phase diagram. The YAP and Alumina XRD peaks were identified from (Jun Wang, 2009) and (Pooya Azadi, 2012) respectively. Thus the CZ method is able to "pull" a pure YAG phase from a highly off stoichiometric melt and leave behind excess oxides.

Photoluminescence (PL) was measured using a Horiba Jobin Yvon Fluorolog-3® Spectrofluorometer with a deuterium arc lamp for excitation down to 180 nm, which allows for a rough quantification of optically active point defects. Analysis was performed with the 1 mm samples at 190 nm excitation at room temperature where 190 nm light provided the brightest hard UV illumination. It is important to note that 190 nm excitation is non-ionizing for YAG. However, as described elsewhere, electrons excited by 230 nm light and below have non-negligible probabilities of escaping the Ce ion and producing characteristics of ionizing radiation, thus providing an indication of behavior to come under gamma excitation.

Figure 5:
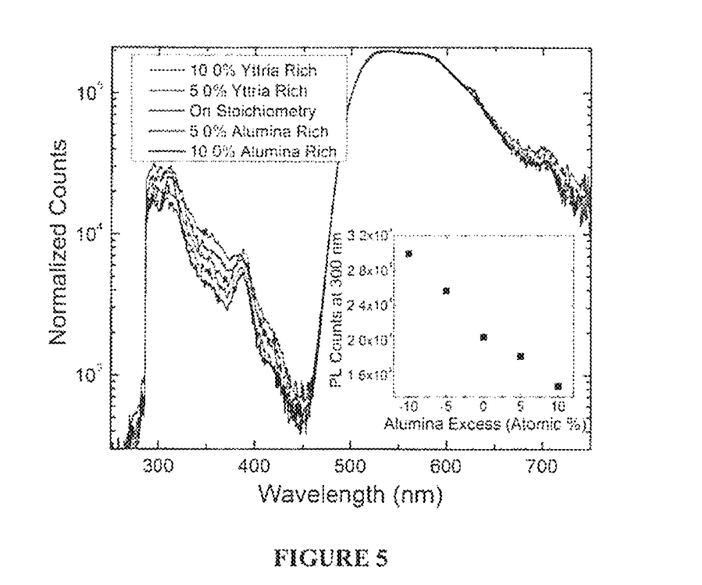
FIG. 5—PL from 190 nm excitation. Barring a small bump in the 10.0 at. % alumina rich sample, and the 380 nm peak due to a doubling reflection of the 190 nm excitation source, the peak centered around 300 nm decreases in a near linear fashion as alumina concentration is increased. Wavelengths below 285 nm are not calibrated, resulting in a sharp drop.

The results in FIG. 5 illustrate the surprising novel result of a clear trend of decreasing UV emission with increasing alumina content in the melt. In fact, the decrease in the 300 nm peak height was nearly linear. This consistency in UV reduction was present across nearly the entire peak range. Since $Y_{Al}^{3+}$ antisites are widely considered to be the source of UV defect emission, the decrease in UV defect emission can be taken to represent a ~30% decrease of $Y_{Al}^{3+}$ antisites in the 10.0 at. % alumina rich melt from the on stoichiometric melt.

Figure 6:
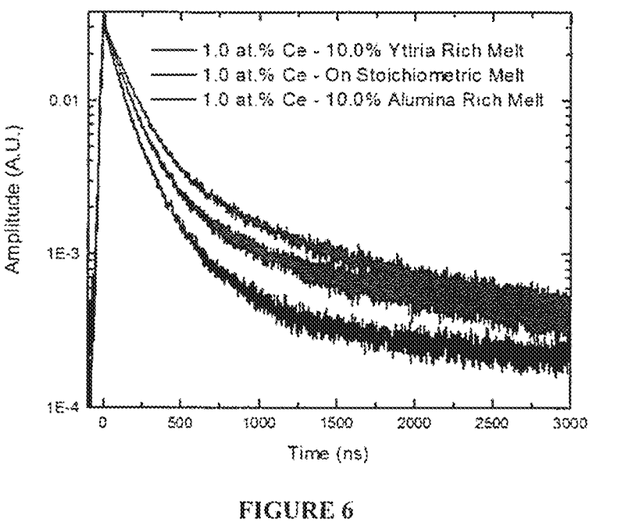
FIG. 6—Lifetime data displaying a significant and consistent decrease in the fast decay component of Ce:YAG as the melt shifts toward alumina rich. An alumina rich melt displays the shortest lifetime (105 ns) with least long components.

Lifetime measurements were performed with the Ø10 mm by 10 mm samples to further investigate the change in $Y_{Al}^{3+}$ antisites. Data was taken using a Photonis XP2020 PMT coupled to a Tektronix MSO 4104 oscilloscope with the samples excited by a $^{137}$Cs gamma source (FIG. 6). A PMT was used in the measurement due to electronic timing constraints. Although this will produce accurate lifetimes, intensity values will have a significant amount of error due to its spectral sensitivity and will not be discussed. A three lifetime fit was taken using the following equation:

$$y = A1 \exp\left(-\frac{x}{t1}\right) + A2 \exp\left(-\frac{x}{t2}\right) + A3 \exp\left(-\frac{x}{t3}\right) + y0$$

Since slow lifetime components have been shown to result from UV defect emission within Ce:YAG, a change in $Y_{Al}^{3+}$ antisites should manifest as a change in decay times. In particular, a reduction in $Y_{Al}^{3+}$ antisites and corresponding UV emission should result in quicker decay times with less contribution from long decay components, which is exactly what was seen in the lifetime figure. The sample from an on stoichiometric melt had a fast decay component of 121.3±0.4 ns, whereas the 10.0 at. % yttria rich melt sample slowed to 155.6±0.4 ns, and the 10.0 at. % alumina rich sample sped up to 98.4±0.5 ns. This is strongly indicates more charge carriers making their way to luminescence centers, as well as less self-absorption of UV emission as $Y_{Al}^{3+}$ antisites are reduced.

Thermoluminescence (TL) was measured with the Ø10 mm by 10 mm samples to investigate their potential role with above room temperature traps. Each sample was deglowed to a temperature of 425° C. then solarized (excited) with a xenon lamp for 20 minutes. After excitation, TL from the samples was measured from room temperature to 400° C. at a heating rate of 12° C./min. TL emission was integrated over the Ce$^{3+}$ emission band of 500-650 nm and the UV emission band from 200-400 nm. The resulting glow curves from each sample can be seen in FIG. 7a (Ce$^{3+}$ emission) and FIG. 7b (UV emission).

Figure 7A:
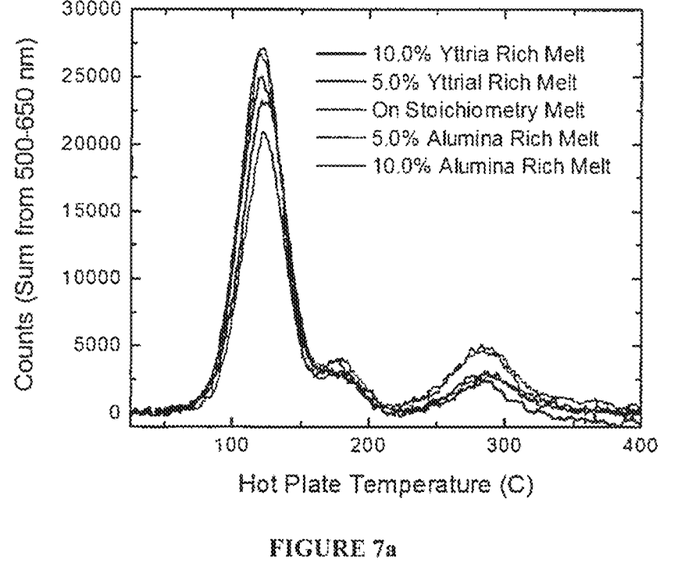
FIG. 7a: Glow curve of each sample from 500-650 nm. The spectrometer exhibited some drift, and although small, is evident at above 300° C.

The Ce$^{3+}$ emission glow curve revealed 3 distinct glow peaks with the peak maximums occurring at temperatures ($T_m$) of 122° C., 178° C., and 285° C. which represented different trapping depths. Each peak was a near Gaussian which is indicative of second order trapping kinetics. An interesting result was the slight increase in counts at all trapping levels as the melt moves toward the alumina rich.

Figure 7B:
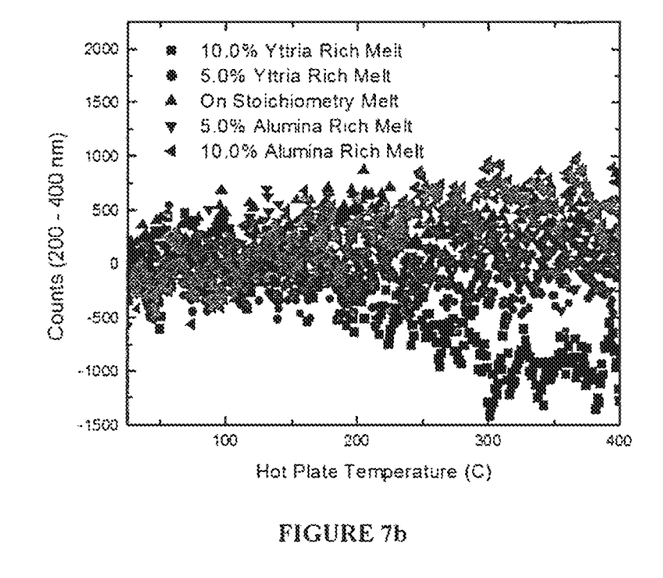
FIG. 7b—TL sum from 200-400 nm. No signal can be seen above background noise. There is a small deviation from a zero average due to spectrometer drift in some samples. The small drift can be seen at higher temperatures in FIG. 7a as well.

In the UV glow curve on the other hand, no signal was evident above background noise and spectrometer drift. Clearly then, thermally released charge carriers are unable to make a radiative recombination through $Y_{Al}^{3+}$ antisites regardless of concentration, though a non-radiative transition is still possible. This strongly suggests thermally activated electrons or holes are not transferring to the conduction or valence band respectively where one should see both UV and visible emission, but are undergoing thermally assisted tunneling to nearby recombination centers.

These observations indicate that as $Y_{Al}^{3+}$ antisites are reduced (as PL and Lifetime data demonstrate) thermally released charge carrier recombination at Ce$^{3+}$ luminescence centers become more probable than non-radiative transfer through $Y_{Al}^{3+}$ centers and this results in higher TL counts in alumina rich melts. A reduction in $Y_{Al}^{3+}$ should also result in more yellow emission and less UV emission under ionizing radiation, which can be investigated through scintillation data.

Figure 8:
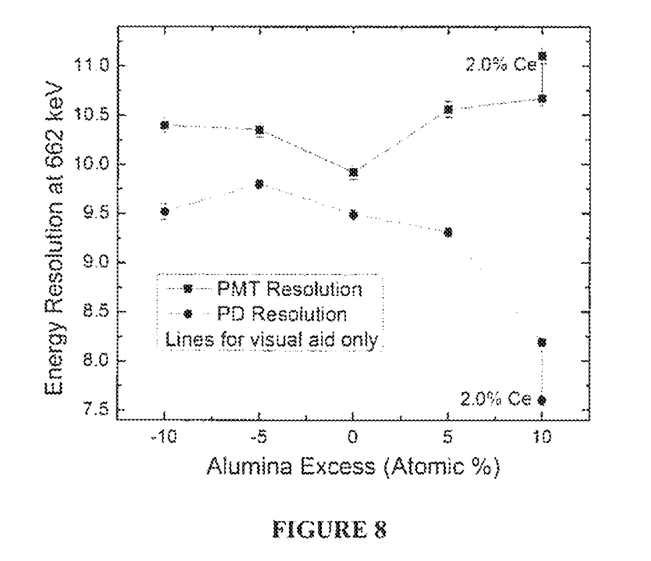
FIG. 8—Scintillation results of all samples on a PMT and PD. Alumina rich samples show excellent consistency between the PMT and PD; however, the trend breaks down with the yttria rich samples. Adding more Ce takes further advantage of an alumina rich melt.

The Ø10 mm by 10 mm right cylinders were wrapped in Teflon tape and coupled to a Photonis XP2018B® photo multiplier tube (PMT) with optical grease so a $^{137}$Cs spectrum to measure scintillation performance and energy resolution could be recorded. Two µs shaping time provided the best resolution with each crystal. As can be seen in FIG. 8, it appears that any deviation from stoichiometry was detrimental to energy resolution measured by the PMT, although the change was more significant in the alumina rich melt.

To test any shift in light output, a 10×10 mm square Hamamatsu S3590-18 photodiode (PD) was also used to obtain a $^{137}$Cs spectrum as previously employed by our group. As per manufacturer's specifications, the PMT had a quantum efficiency (QE) of 23.1% at a wavelength of 300 nm, but a QE of <4.9% at 550 nm and above, where the scintillation emission is supposed to occur. The S3590-18 PD on the other hand, had a QE of >85% between 420-800 nm (90% at 550 nm) and a QE<<10% (undefined) at wavelengths of <300 nm.

Results obtained with the S3590-18 PD are compared to the PMT in FIG. 8 and Table I. Two µs shaping provided the best resolution, where the PD displayed a remarkable trend toward better energy resolutions with an alumina rich melt and was consistent with the PL data. Such a dramatic improvement on the PD (visible sensitive) and degradation on the PMT (UV sensitive) strongly suggests $Y_{Al}^{3+}$ antisite concentrations are reduced resulting in increased 550 nm emission due the alumina rich melts. The greatest change occurred in the 10.0% alumina rich melt, where the 10 mm thick as grown sample displayed an impressive resolution of 8.2±0.04% on a PD.

To investigate alumina rich melts further, a crystal was grown with 2.0 at. % Ce in a 10.0% alumina rich melt (the highest Ce and alumina rich melt that can be grown well) under the same growth conditions described earlier. As determined in our previous work, higher Ce concentrations also led to reduced UV luminescence and increased visible emission through improved competition between Ce and $Y_{Al}^{3+}$ luminescence centers. If $Y_{Al}^{3+}$ defects are in fact reduced in an alumina rich melt, then there is no reason the effects cannot be cumulative and result in further reduced UV emission and further increased visible emission.

When tested on a PMT and PD, this is exactly what was observed. The 2.0 at. % Ce sample is included in FIG. 8, and showed further improvement in resolution on a PD (7.6±0.05%) and degradation on a PMT (11.1±0.08%). A pulser was used to decouple true energy resolution from the electronic noise inherent in Si-PIN PD's and is described elsewhere. The true energy resolution with noise subtracted was calculated to 5.04±0.07%.

Figure 9:
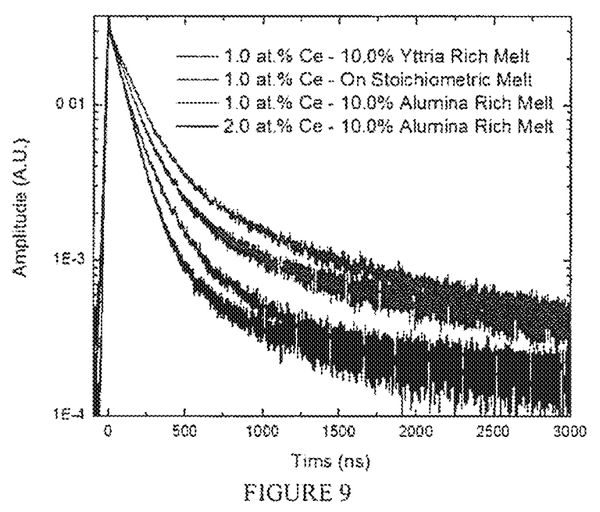
FIG. 9—Lifetimes along with the 2.0 at. % Ce:YAG sample grown from a 10.0 at. % alumina rich melt. Increased Ce further improves the lifetimes seen earlier.

Lifetime was measured with the sample in the same manner as described earlier and can be seen in FIG. 9. As seen in earlier measurements, growth in higher alumina concentrations results in fewer yttrium antisite defects and higher cerium concentrations further mitigates their effects. Accordingly, the fast decay was surprisingly reduced to 84.7±0.5 ns.

Figure 10:
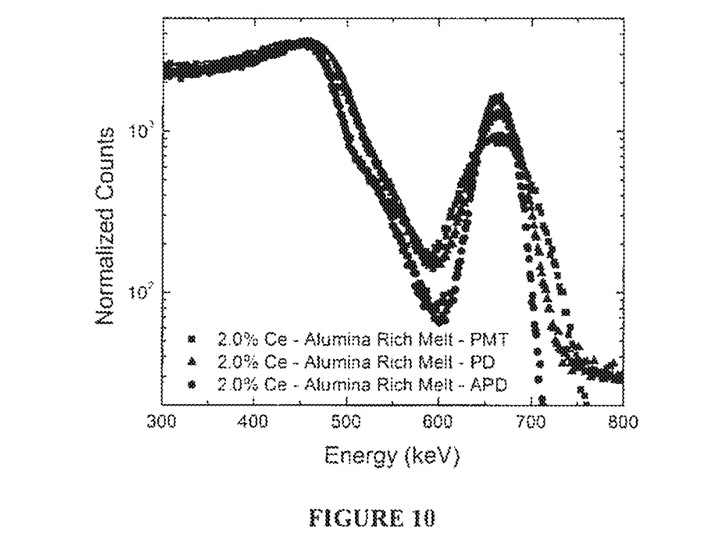
FIG. 10—APD, PD, and PMT results from the 2.0 at. % Ce, 10% alumina rich melt grown sample. The PD photopeak is visibly narrower than the PMT's even with the inherent noise of a Si-PIN PD. The APD photopeak is even narrower. Such results indicate a significant gain in visible emission from alumina rich growth conditions.

The above lifetime and energy resolution measurements were verified by measuring the 2.0 at. % Ce, 10.0 at. % alumina rich sample on a Hamamatsu S8664-1010 avalanche photodiode (APD). Although the quantum efficiency of 75-85% from 450-800 nm is slightly less than the Hamamatsu S3590-18 PD, it does provide signal gain and thus has significantly less noise. The results can be seen with the PD and PMT spectra in FIG. 10 and Table II, where the best spectrum was recorded with 0.75 µs shaping, which was a result of the faster lifetime seen in FIG. 9. A value of 5.9±0.02% (5.5±0.03% with noise subtraction) confirmed the PD results. These results are unmatched by any previous results on a PMT, PD, or even APD, for as grown Ce:YAG of this size.

TABLE II

Energy resolution comparison of the 2.0 at. % Ce, 10.0 at. % alumina rich sample.

| Energy Res. (%) | PMT | PD | APD |
| --- | --- | --- | --- |
| No Noise Reduction | 11.1 ± 0.08 | 7.6 ± 0.05 | 5.9 ± 0.02 |
| With Noise Reduction | No Sig. Noise | 5.04 ± 0.07 | 5.5 ± 0.03 |

A final study was carried out to investigate the nature of change in $Y_{Al}^{3+}$ antisites. The 5.0 at. % yttria rich melt, 5.0 at. % alumina rich melt, and on stoichiometry melt grown samples underwent an anneal and aluminum in diffusion process as described in (D. Solodovnikov, 2008). These samples were chosen because they had the most similar growth conditions experienced by the sample in (D. Solodovnikov, 2008), where small deviations in melt stoichiometry (toward yttria rich) were likely. Each of the samples demonstrated negligible differences in scintillation performance compared with the as grown results. This is in stark contrast to Solodovnikov et al which demonstrated a remarkable increase in UV emission and decrease in visible emission due to a modification of antisite-vacancy complexes. This strongly demonstrated that the samples from this study were not altering antisite-vacancy complexes, but were in fact altering $Y_{Al}^{3+}$ antisites alone through adjustment of the growth conditions.

Without a doubt, Ce:YAG grown from a highly alumina rich melt works to reduce the concentration of $Y_{Al}^{3+}$ antisites along with their corresponding defect emission, and increase visible emission. A highly doped sample further mitigates their negative influence. Together, the two methods provide novel excellent results even with larger sample sizes.

In conclusion, Ce:YAG grown from an alumina rich melt appears to be an effective method of reducing $Y_{Al}^{3+}$ antisite concentrations and hence UV defect emission as seen by PL. This in turn increases visible light output and results in record performing Ce:YAG scintillators on cost effective PD's. Future work will investigate light yield in both the UV and visible spectrums in these and other sample. At present, an off stoichiometry alumina rich melt provides a new method for further improving visible light emission in Ce:YAG, and demonstrates potential as a cost effective scintillator in commercial systems.

We claim:

1. A luminescent inorganic material comprising $Y_{3-x}M_xAl_{5+y}O_{12+z}$, wherein $0 \le x < 0.03$, $0.001 < y < 0.2$ and $0 < z < 0.012$ and M is selected from, cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu) or combinations thereof.

2. The material of claim 1 wherein X=0.

3. The material of claim 1 wherein M is Ce.

4. A method of forming a luminescent inorganic material comprising:
   (a) providing a mixture of $Y_2O_3$, and $Al_2O_3$ in a Y:Al molar ratio of between 1.5:2.5 and 1.5:2.75;
   (b) heating the mixture to a liquid state; and
   (c) solidifying the mixture to form the compound.

5. The method of claim 4, wherein the method enables the reduction of the frequency of $Y^{3+}{}_{Al}$ antisites.

6. The method of claim 4 wherein a metal oxide dopant is included in the mixture in a Y:M molar ratio of between 1.5:0.0015 and 1.5:0.15 and M is selected from cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), Chromium (Cr) and lutetium (Lu) or combinations thereof.

7. The method of claim 4 wherein M is cerium (Ce).

* * * * *